United States Patent
Weltmann et al.

(10) Patent No.: US 10,363,429 B2
(45) Date of Patent: Jul. 30, 2019

(54) DEVICE FOR THE PLASMA TREATMENT OF HUMAN, ANIMAL OR PLANT SURFACES, IN PARTICULAR OF SKIN OR MUCOUS MEMBRANE AREAS

(71) Applicant: Leibniz-Institut für Plasmaforschung und Technologie e.V., Greifswald (DE)

(72) Inventors: Klaus-Dieter Weltmann, Binz (DE); Ronny Brandenburg, Gross-Kiesow (DE); Stephan Krafczyk, Greifswald (DE); Manfred Stieber, Greifswald (DE); Thomas Von Woedtke, Sundhagen (DE)

(73) Assignee: Leibniz-Institut für Plasmaforschung und Technologie e.V., Greifswald (DE)

( * ) Notice: Subject to any disclaimer, the term of this patent is extended or adjusted under 35 U.S.C. 154(b) by 894 days.

(21) Appl. No.: 14/399,840

(22) PCT Filed: May 8, 2013

(86) PCT No.: PCT/EP2013/059656
§ 371 (c)(1),
(2) Date: Nov. 7, 2014

(87) PCT Pub. No.: WO2013/167693
PCT Pub. Date: Nov. 14, 2013

(65) Prior Publication Data
US 2015/0088234 A1    Mar. 26, 2015

(30) Foreign Application Priority Data

May 9, 2012   (DE) .................. 10 2012 207 750

(51) Int. Cl.
*A01G 7/04*   (2006.01)
*A61N 1/44*   (2006.01)
(Continued)

(52) U.S. Cl.
CPC ................ *A61N 1/44* (2013.01); *A01G 7/04* (2013.01); *A61B 18/042* (2013.01);
(Continued)

(58) Field of Classification Search
CPC ........ A61B 2018/00583; A61B 18/042; H05H 2001/2412; A05H 1/2406
See application file for complete search history.

(56) References Cited

U.S. PATENT DOCUMENTS 5,047,026 A * 9/1991 Rydell ............... A61B 18/1482
606/39
6,494,881 B1   12/2002 Bales et al.
(Continued)

FOREIGN PATENT DOCUMENTS

DE        3618412        12/1987
DE     60021083 T2        5/2006
(Continued)

OTHER PUBLICATIONS

International Search Report dated Oct. 9, 2013, in PCT/EP13/059656 filed May 8, 2013.
(Continued)

*Primary Examiner* — Kaitlyn E Smith
(74) *Attorney, Agent, or Firm* — Soroker Agmon Nordman

(57) ABSTRACT

The invention relates to a device for the treatment of free-form areas and zones of human or animal skin areas or plant surfaces by means of cold atmospheric-pressure plasma. The core of the device is a specific, preferably gas-permeable, electrode arrangement for generating a dielectrically impeded surface discharge where the earthed electrode is composed of electrically conductive textile material and the high-voltage electrode consists of a thin wire or electrically conductive thread which is sheathed with (Continued)

Figure 1:
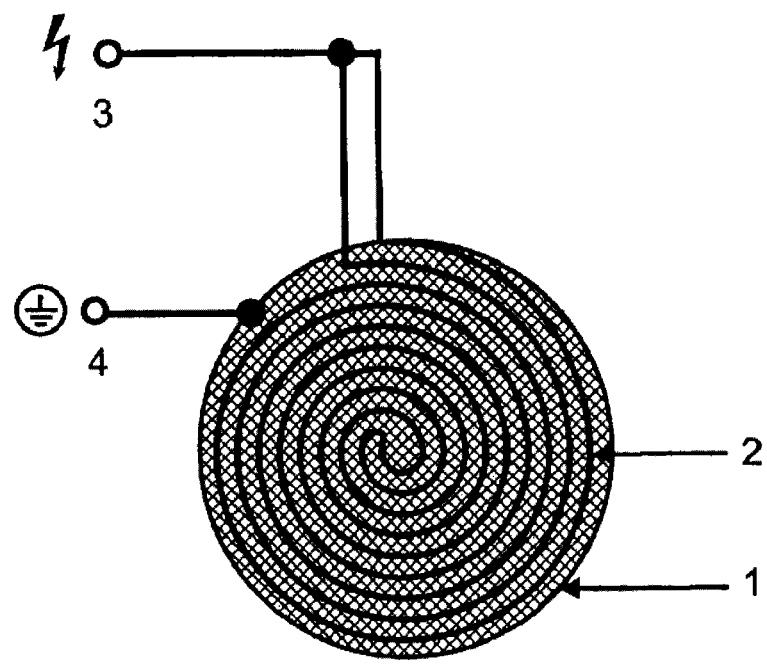

an insulting layer which has to meet specific requirements. On the basis of the present invention, it is possible to generate, in the area of diseased skin parts of the human body, in direct proximity to the skin surface or to wounds, a flat plasma for the treatment of the diseased areas which is acceptable in respect of the stress on the skin caused by temperature and electric potentials. The advantage of the gas-permeable textile sheet-like structure consists especially in that the arrangement can be placed flexibly onto variously curved surfaces and, in addition, offers the possibility of a gas exchange with the environment and/or the targeted dosing of a specific process gas mixture across the textile material into the active plasma zone.

15 Claims, 2 Drawing Sheets

(51) Int. Cl.
  *H05H 1/24* (2006.01)
  *A61B 18/00* (2006.01)
  *A61B 18/04* (2006.01)
(52) U.S. Cl.
  CPC . *H05H 1/2406* (2013.01); *A61B 2018/00065* (2013.01); *A61B 2018/00136* (2013.01); *A61B 2018/00452* (2013.01); *H05H 2001/2412* (2013.01)

(56) References Cited

U.S. PATENT DOCUMENTS

| 2004/0249041 | A1* | 12/2004 | Meloni | C08K 9/04 524/430 |
|---|---|---|---|---|
| 2005/0288665 | A1* | 12/2005 | Woloszko | A61B 18/1482 606/41 |
| 2008/0039832 | A1* | 2/2008 | Palanker | A61B 18/042 606/39 |
| 2009/0054896 | A1* | 2/2009 | Fridman | A61B 18/042 606/49 |
| 2011/0116967 | A1 | 5/2011 | Roy et al. | |
| 2012/0107896 | A1 | 5/2012 | Wandke et al. | |
| 2012/0271225 | A1 | 10/2012 | Stieber et al. | |
| 2017/0136252 | A1* | 5/2017 | Weltmann | A61N 1/44 |
| 2017/0216614 | A1* | 8/2017 | Weltmann | A61N 1/44 |

FOREIGN PATENT DOCUMENTS

| DE | 69928370 T2 | 8/2006 |
|---|---|---|
| DE | 10 2008 045 830 A1 | 3/2010 |
| DE | 102008045830 A1 | 3/2010 |
| DE | 102009002278 A1 | 10/2010 |
| EP | 1300439 A1 | 4/2003 |
| EP | 1158919 B1 | 6/2005 |
| EP | 1027020 B1 | 11/2005 |
| JP | 201261393 A | 3/2012 |
| WO | 2010094304 A1 | 8/2010 |
| WO | WO 2011/023478 A1 | 3/2011 |

OTHER PUBLICATIONS

Fridman G. et al., "Sterilization of Living Human and Animal Tissue by Non-Thermal Atmospheric Pressure Dielectric Barrier Discharge Plasma" ISPC 18. Kyoto 2007; Fridman G. et al. Plasma Chemistry and Plasma Processing 2006, 26, 425-442; Fridman G. et al. "Applied Plasma Medicine", Plasma Process. Polym. 2008, 5, 503-533).

* cited by examiner

DEVICE FOR THE PLASMA TREATMENT OF HUMAN, ANIMAL OR PLANT SURFACES, IN PARTICULAR OF SKIN OR MUCOUS MEMBRANE AREAS

The invention relates to a device for the treatment of freeform surfaces and zones of human or animal skin areas as well as plant surfaces by means of a cold atmospheric-pressure plasma.

PRIOR ART

Numerous investigations on the applicability of atmospheric-pressure plasmas for medical therapeutic purposes are now described in the literature on the new "Plasma medicine" discipline (For example: Fridman G. et al., "Sterilization of Living Human and Animal Tissue by Non-Thermal Atmospheric Pressure Dielectric Barrier Discharge Plasma" ISPC 18. Kyoto 2007; Fridman G. et al. "Blood Coagulation and Living Tissue Sterilization by Floating-Electrode Dielectric Barrier Discharge in Air", Plasma Chemistry and Plasma Processing 2006, 26, 425-442; Fridman G. et al. "Applied Plasma Medicine", Plasma Process. Polym. 2008, 5, 503-533).

In order that innovative methods of this kind can be developed and applied, it is necessary to develop special atmospheric-pressure plasma sources, which must satisfy a series of conditions. For example, if such a plasma source is to be used in the context of a medical therapeutic strip, the following prerequisites must be met:

(1) The sources should be suitable for defined, reproducible, superficial treatment of arbitrarily curved areas of skin or mucous membrane or plant surfaces.
2) The sources should be made of flexible materials, which can be autoclaved and are chemically resistant as well as plasma-resistant.
(3) The materials used should be biocompatible.
(4) The sources should permit painless treatment, which does not damage the tissue to be treated either due to heat, desiccation and the effect of electrical fields or due to the effect of reactive species generated by the plasma.
(5) Metered supply of a special process-gas mixture should be possible, if necessary with admixture of further substances, not only under conditions of a continuous gas stream but also in a closed volume.
(6) Optionally, the electrode arrangement of the plasma source should be structured such that it is permeable to gas and so a gas stream onto the surface to be treated can be generated through the electrode arrangement.
(7) The sources should be simply structured, to permit industrial production that is as simple and inexpensive as possible.

Heat-resisting, biocompatible and chemically resistant plastics are known to the person skilled in the art.

The devices described in patents DE3618412, WO2004/105810 and WO2006/116252 for plasma treatment of living tissue with non-thermal atmospheric plasmas are equipped either with rigid electrode systems (DBD electrodes) for local treatment of small areas or with "plasma nozzles" (plasma jets) for generation of atmospheric-pressure plasmas in the zone of the tissue surfaces to be treated. Their use for short-time, defined and reproducible treatment of larger skin zones must therefore be regarded as problematic.

In an earlier patent of the inventor (WO2011/023478 A1), a device with a special elastic electrode arrangement, for generation of a superficial plasma by means of a dielectrically hindered surface discharge, which can be applied flexibly to arbitrarily curved surfaces and thus is suitable in principle for plasma treatment of diseased skin areas, was described as a suitable option for superficial treatment of biological tissue by means of a cold atmospheric-pressure plasma. A disadvantage in this case is the fact that some of the above-mentioned prerequisites (especially prerequisites (2), (6) and (7)) are not met with atmospheric-pressure plasma sources of this kind.

Document DE 102008045830 A1 (CINOGY GmbH), also published as US 2012107896 A1 or WO 2010/025904 A2, also belongs to the prior art. Therein it is disclosed that a device for treatment of surfaces is used that, by means of an electrode above a solid-state dielectric, generates a plasma by a dielectrically hindered gas discharge, wherein the device has an active surface that can change shape reversibly and that directly adjoins the plasma during the treatment. In the description, it is mentioned in paragraph [0024]: " . . . that the dielectric has the form of granules and/or powder. This may also be achieved, however, by the fact that the dielectric is disposed, for example as fine powder, on and/or in a flexible hollow fiber, for example of glass, ceramic or plastic, or that the dielectric itself is a flexible hollow fiber." In paragraph [0068], it is further stated that "several hollow fibers of dielectric material or with a dielectric coating of glass, ceramic or plastic and equipped with electrodes, for example in the form of an internal coating in combination with further bracing elements in the form of fibers, constitute a tissue-like element, so that appropriately adequate and adapted shaping and thus application is possible even in the case of complex topologies." However, a dielectric strength of at least 2 kV is not described therein for the dielectric. Neither is any polyimide, silicone or aramide disclosed.

In European Patent EP 1027020 B1 it is described that a plasma intense enough to achieve tissue ablation is generated with a compact, rod-like (not superficial) bipolar electrode system in a conductive liquid environment (electrolyte, e.g. NaCl solution). A "breakdown voltage" of at least 2 kV is indeed mentioned therein, but the overall arrangement is directed toward working in the presence of an electrically conductive fluid.

Finally, publications DE 102009002278 A1 and EP 1158919 B1 must also be mentioned briefly here. DE 102009002278 A1 describes a DBD arrangement that has already been known for 150 years, besides other known principles, with an ultrasonic source. In EP 1158919 B1, a method for treatment of skin or tissue is disclosed.

OBJECT OF THE INVENTION

The object of the invention is to find a technical solution for the construction of a plasma source that satisfies the prerequisites mentioned hereinabove.

ACHIEVEMENT OF THE OBJECTIVE

The object is achieved by the features of the claims.

DESCRIPTION OF THE INVENTION

According to the invention, a special electrode arrangement is used in which the high-voltage electrode consists of a thin wire or electrically conductive filament, which is sheathed with an insulating layer that has a high dielectric strength or breakdown voltage, exhibits thermal stability sufficient for autoclaving capability and is chemically resistant, biocompatible and plasma-resistant. Insulating materials with these special properties are limited to a few types of plastics. Example thereof are listed in the following table:

TABLE 1

Properties of materials with high dielectric strength

| Plastics | Dielectric constant | Dielectric strength [kV/mm] | Max. temperature [° C.] |
| --- | --- | --- | --- |
| Silicones (e.g. Silastic ®, Elastosil ®) | 2-3 | up to 40 | 150-350 (highly heat-resistant silicone) |
| Polyimides (e.g. Kapton ® CR (durably plasma-resistant)) | 3.4 | up to 45 | 220-260 (briefly: 400) |
| Aramides (e.g. Kevlar ®, Nomex ®) | 3.2 | 18 to 40 | 220 |

An essential feature for the suitability of the insulation under these conditions is the property characterized as "plasma-resistant". Whereas the material properties of most insulating materials are influenced by the reactive species generated in the plasma to the effect that the insulation becomes brittle during continuous use and thereby the dielectric strength is impaired, the material properties of Kapton, for example, remain stable. For the inventive device, this means that polyimides, preferably aromatic polyimides, e.g. known as Kapton®, chemical name poly(4,4'-oxydiphenylene-pyromellitimide), which are the most suitable insulating materials for the insulation of thin conductive filaments or of the wire, are especially suitable for prolonged treatment of surfaces. Plastics suitable for a shorter duration of use include silicone, aramides (aromatic polyamides) or fluoropolymer working materials such as FEP, PFA, ETFE, PTFE, especially Teflon®, the material properties of which under plasma conditions can indeed be regarded as stable for a limited time, but not as durably stable. The decisive electrical variable for the insulating layer used for high-voltage electrodes is the breakdown voltage, which depends on the one hand on the material characteristic of dielectric strength (kV/mm) and on the other hand on the thickness of the insulating layer. According to the invention, the breakdown voltage of the high-voltage electrode is at least 2 kV, preferably 5-10 kV.

Good results are achieved with polyimides, such as poly-bismaleimide (PBMI), polybenzimidazole (PBI), polyoxadi-azobenzimidazole (PBO), polyimide sulfone (PISO) and polymethacrylimide (PMI). Aromatic polyimides, such as poly(4,4'-oxydiphenylene-pyromellitimide) are preferred. The best results are achieved when the aromatic polyimide additionally contains an inorganic filler. Such a material is known under the brand name "Kapton® CR" of DuPont. Inorganic fillers in electrical solid-state insulators based on a thermosetting plastic matrix are known from laid-open patent application EP 1300439 A1. Among others they include silicon dioxide, aluminum dioxide, titanium dioxide or dolomite ($CaMg[CO_3]_2$). The use of ATH (aluminum trihydrate) is also known.

According to the invention, mixed polymers of polyimides, silicone, fluoropolymers or aramides may also be used. According to the invention, it is also possible to coat the wire or the filaments with several polymers, e.g. a base coat of polyimides and a further coat of silicone or vice versa, depending on the desired flexibility.

In contrast to DE 102008045830 A1, the plasma arrangement represents a form-fitting structure. The shape of the active surface does not change, since the dielectric is not deformed. Furthermore, no additional bracing element is needed, but instead the system is already stable enough. A further difference is the textile variants of the plasma source.

The grounded electrode for generation of a dielectrically hindered surface discharge does not absolutely have to be permeable to gas. For certain applications, e.g. therapies in which extra-impermeable sealing against air is used, a microclimate is required. In the case of use of a gas-permeable electrode, this may also be achieved by applying an additional layer or film that is impermeable to gas as the seal against the external atmosphere, or by means of a gas-tightly closed housing, which if necessary can be connected to a gas line with shutoff capability.

According to a preferred embodiment of the invention, however, a gas-permeable grounded electrode is used for generation of a dielectrically hindered surface discharge from electrically conductive textile material.

The centerpiece of the inventive embodiment is a special, preferably gas-permeable electrode arrangement for generation of a dielectrically hindered surface discharge, in which preferably the grounded electrode consists of electrically conductive material and the high-voltage electrode consists of a thin wire or electrically conductive filament, which is sheathed with an insulating layer, which must satisfy special requirements. On the basis of this invention, it is possible to generate, in the zone of diseased skin parts of the human body, in immediate proximity to the skin surface or to wounds, a superficial plasma for treatment of diseased areas that is safe in terms of exposing the skin to heat and electrical voltages. The advantage of the gas-permeable textile flat structure consists mainly in the fact that the arrangement can be applied flexibly on arbitrarily curved surfaces and beyond this offers the possibility of gas exchange with the surroundings or selective metering of a special process-gas mixture through the textile material into the active plasma zone.

Plants (trees) also have wounds. Appropriate application procedures are available with the inventive device, especially for useful plants.

EXAMPLES

The invention will be explained in more detail on the basis of exemplary embodiments.

Figure 2:
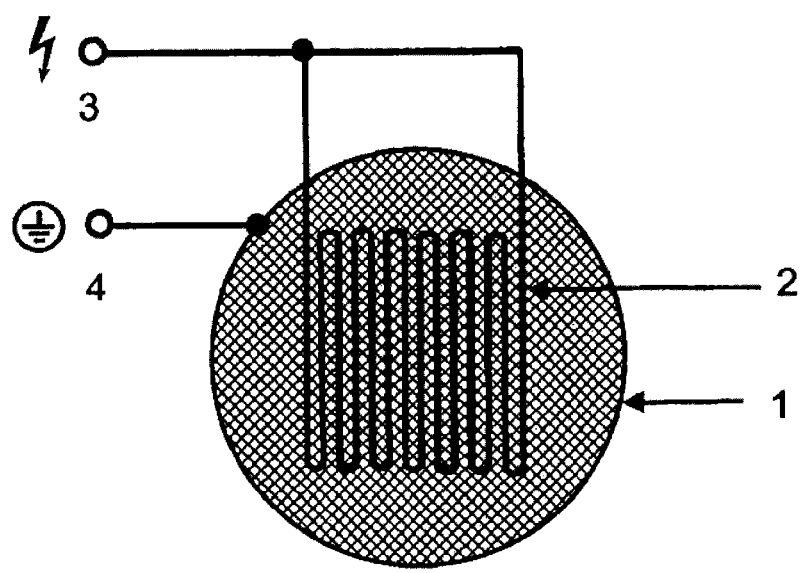

For this purpose, FIG. 1 and FIG. 2 show schematic diagrams of functional models of the inventive device. The difference between these two examples consists in the arrangement of the high-voltage electrode of insulated wire on the electrically conductive textile material used as the grounded electrode. In FIG. 1 the high-voltage electrode is disposed as a spiral, whereas in FIG. 2 a meandering arrangement of the high-voltage electrode is illustrated.

Figure 3:
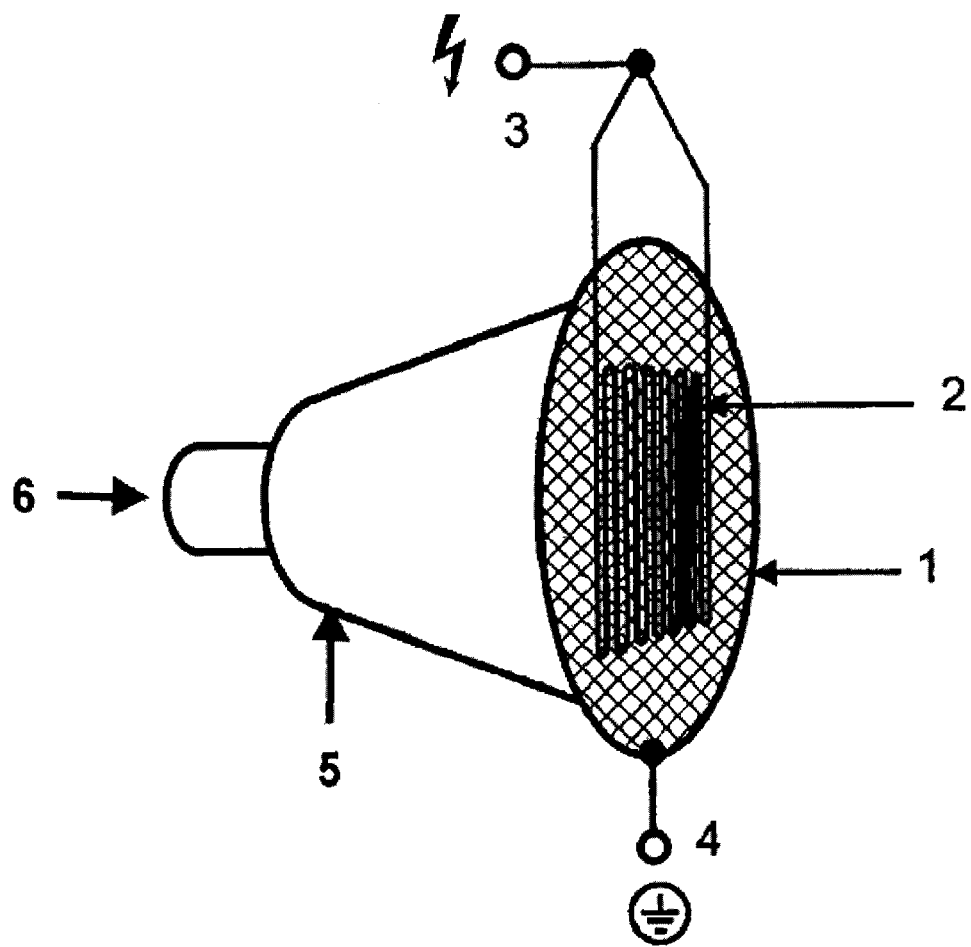

FIG. 3 shows the basic layout of a variant of the inventive device, in which the possibility of metered supply of a special process-gas mixture, if necessary with admixture of further substances, can be realized by the gas-permeable electrode arrangement.

LIST OF REFERENCE SYMBOLS

The following reference symbols are used for the attached drawings:

1 Grounded electrode of conductive woven material (e.g. of conductive textile material)
2 High-voltage electrode of insulated wire with insulation of heat-resisting and plasma-resistant as well as chemically resistant insulating material with high dielectric strength (e.g. Kapton® CR)

3 High voltage cable
4 Ground cable
5 Gas nozzle
6 Gas supply

The invention claimed is:

1. A device for a treatment of a zone of a human or an animal or a plant surface or area by a cold atmospheric-pressure plasma by generation of a dielectrically hindered surface discharge, the device comprising:
   at least one high-voltage cable,
   at least one ground cable,
   at least one grounded electrode, and
   at least one high-voltage electrode,
   wherein the at least one high-voltage electrode consists of a single sheathed flexible wire or a single sheathed electrically conductive filament having an elastic insulating layer as a sheath, and
   wherein the sheathing insulation layer is used as a dielectric to generate a dielectrically hindered discharge which at the same time conforms to the contour of the surface or area to be treated and has a dielectric strength of at least 2 kV.

2. The device according to claim 1, wherein a silicone, a fluoropolymer, an aramide, or a polyimide, which encloses the at least one high-voltage electrode, is used as the insulating layer for the at least one high-voltage electrode.

3. The device according to claim 2, wherein an aromatic polyimide is used.

4. The device according to claim 3, wherein the aromatic polyimide comprises inorganic fillers.

5. The device according to claim 3, wherein poly(4,4'-oxydiphenylene-pyromellitimide) and inorganic fillers is used as the insulating layer.

6. The device according to claim 3, wherein the aromatic polyimide is poly(4,4'-oxydiphenylene-pyromellitimide).

7. The device according to claim 1, wherein a conductive, gas-permeable and flexible material functions as the at least one grounded electrode.

8. The device according to claim 7, wherein a conductive textile flat structure functions as the at least one grounded electrode, and wherein the conductive textile flat structure is material woven, weft-knit, braided or warp-knit.

9. The device according to claim 1, further comprising: at least one gas nozzle.

10. The device according to claim 1, wherein the device further comprises at least one gas supply, wherein at least one gas supply is interrupted by a shutoff device, so that the treatment is applied in a closed volume and conditions of a microclimate above the surface to be treated.

11. The device according to claim 1, wherein the at least one sheathed high-voltage electrode and the at least one grounded electrode form an electrode arrangement, wherein said electrode arrangement is permeable to gas such that a gas stream onto the surface to be treated can be generated through the electrode arrangement.

12. The device according to claim 1, wherein the device is formed as a medical strip, a cuff, or a wound covering for application on a skin zone.

13. The device according to claim 1, wherein the zone of a human or an animal or a plant surface or area is an area of skin or a mucous membrane.

14. The device according to claim 1, wherein the device comprises at least one gas supply.

15. A device for a treatment of a zone of a human or an animal or a plant surface or area by a cold atmospheric-pressure plasma by generation of a dielectrically hindered surface discharge, the device comprising:
   at least one high-voltage cable,
   at least one ground cable,
   at least one grounded electrode, and
   at least one high-voltage electrode,
   wherein the at least one high-voltage electrode consists of a sheathed flexible wire or sheathed electrically conductive filament having an elastic insulating layer as a sheath,
   wherein the sheathing insulation layer is used as a dielectric to generate a dielectrically hindered discharge which at the same time conforms to the contour of the surface or area to be treated and has a dielectric strength of at least 2 kV, and
   wherein the sheathed wire or the sheathed electrically conductive filament is arranged free of crossings with itself.

* * * * *